United States Patent
Waldmann

[11] Patent Number: 5,961,543
[45] Date of Patent: Oct. 5, 1999

[54] METHOD AND APPARATUS FOR PHOTODYNAMIC IRRADIATION

[75] Inventor: Gerhard Waldmann, Dauchingen, Germany

[73] Assignee: Herbert Waldmann GmbH & Co., Germany

[21] Appl. No.: 08/742,727

[22] Filed: Nov. 1, 1996

[30] Foreign Application Priority Data

Nov. 8, 1995 [DE] Germany ................ 295 17 716 U

[51] Int. Cl.$^6$ ............................................. A61B 5/00
[52] U.S. Cl. ............................................. 607/88; 606/9
[58] Field of Search ................ 607/88–89, 90; 606/2, 3, 9–13, 17–19; 507/88–94

[56] References Cited

U.S. PATENT DOCUMENTS

| | | | |
|---|---|---|---|
| 4,682,595 | 7/1987 | Hoerenz | 607/89 |
| 5,344,418 | 9/1994 | Ghaffari | 606/9 |
| 5,511,563 | 4/1996 | Diamond | 607/88 X |
| 5,626,631 | 5/1997 | Eckhouse | 607/88 |
| 5,643,333 | 7/1997 | Yun | 607/88 |
| 5,782,895 | 7/1998 | Zarate et al. | 607/88 |

*Primary Examiner*—Jeffrey R. Jastrzab
*Assistant Examiner*—Ryan Carter
*Attorney, Agent, or Firm*—Eugene E. Renz, Jr., PC

[57] ABSTRACT

Apparatus for photodynamic irradiation comprising a housing (10), a lamp (16) mounted in the housing and a reflector (18) surrounding the lamp. A filter unit (40) is mounted in the beam path of the lamp and the reflector, and a light outlet (26) in the housing following the filter unit. A dosage device accurately meters the radiant energy delivered by the apparatus to a patient.

16 Claims, 5 Drawing Sheets

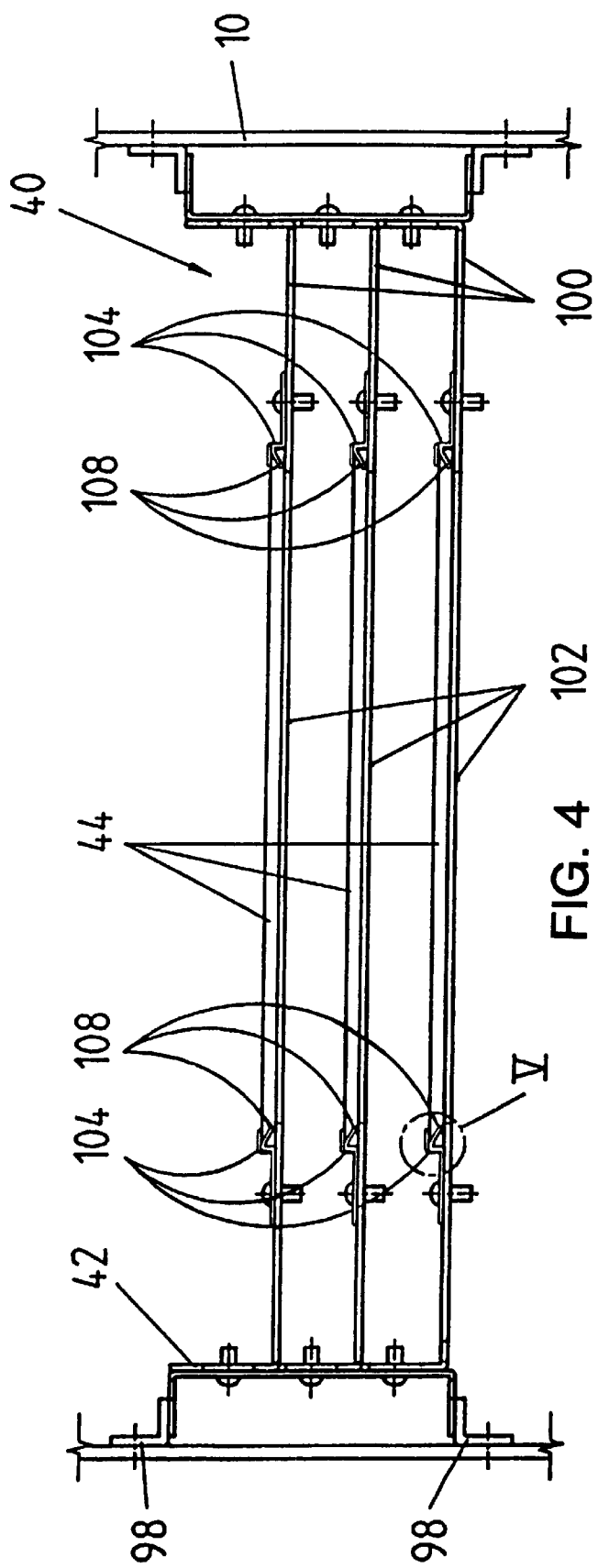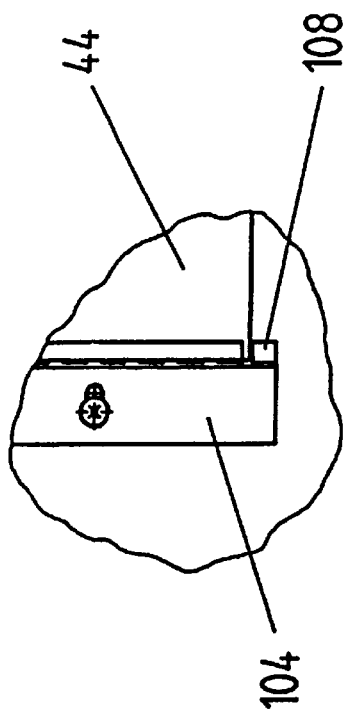
FIG. 4
FIG. 5

METHOD AND APPARATUS FOR PHOTODYNAMIC IRRADIATION

FIELD OF THE INVENTION

The present invention relates to an Apparatus and Method for Photodynamic Irradiation and more specifically to improvements facilitating delivery of precise measured dosages of radiant energy to a patient.

BACKGROUND OF THE INVENTION

Photodynamic Irradiation devices are not new per se. Patients are exposed to photodynamic radiation for therapeutic purposes. A common drawback in devices of this type presently known is that it is not easy to deliver precisely the desired dose of radiant energy to the patients.

SUMMARY OF THE INVENTION

With the foregoing in mind therefore, it is an object of the present invention to provide an improvement in devices of this type which facilitates delivery of the exact dose of radiant energy desired and which at the same time is easy to use and maintain. These apparatus typically comprise a housing, a lamp mounted in the housing, a reflector surrounding the lamp, a filter unit mounted in the beam path of the lamp and a light outlet in the housing downstream of the filter unit. In accordance with the present invention, the system includes a dosage device for accurately metering radiant energy delivered by the apparatus to a patient. Preferably the dosing device consists of diaphragm unit and the path of the beam is controlled by a timer or computer. The diaphragm may be a shutter capable of being moved in the path of the beam or it can have flaps actuatable by a crank mechanism driven by an electric motor to permit the flaps to be swung into the path of the beam. It is also possible to use a timer or a computer to control the limit of time the lamp is on and to measure the dosage. The use of a diaphragm is preferred because the lamp does not have to be turned on or off so frequently and can continue to burn while the diaphragm unit is closed.

In accordance with the another feature of the present invention, it is also possible to install a radiation dosimeter directly at the treatment site, that is on the patient. The dosimeter can be connected with the irradiation system by cable. Accordingly, when the radiation dosimeter measures a predetermined amount of radiant energy delivered which can be determined in advance, it can actuate the dosage device and thus turn off the lamp or block off the energy.

According to another feature of the present invention, means are provided for adjusting the distance between outlet of the apparatus and the treatment site and in this way adjust the intensity of the radiation at the treatment site which is an important aspect for controlling dosage. For example, a distance meter can be used for this purpose.

There are other features of the invention herein set forth which make it possible to use and maintain the apparatus easily and which therefore make it possible to deliver the radiant energy reliably and reproducibly.

BRIEF DESCRIPTION OF THE DRAWINGS

With the foregoing in mind, these and other objects of the present invention and the various features and details of the operations and construction thereof, are hereinafter more fully set forth with reference to the accompanying drawings, wherein;

FIG. 4 is a schematic side elevational diagrammatical, view of the filter unit used in apparatus in accordance with present invention;

FIG. 5 is a large partial view of the detail in FIG. 4D taking in a longitudinal direction in the apparatus.

DETAILED DESCRIPTION OF THE PREFERRED EMBODIMENT

Figure 1:
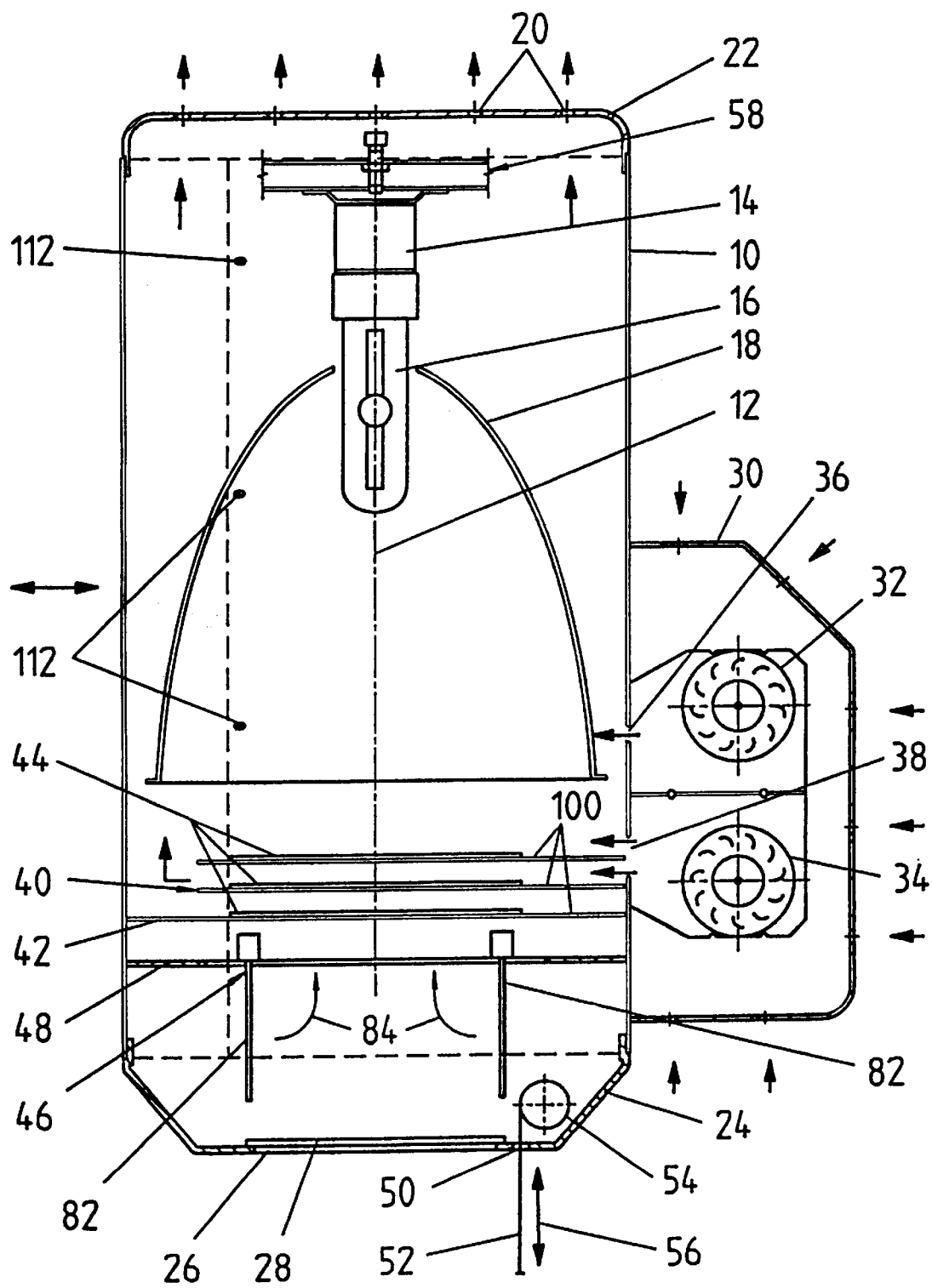
FIG. 1 is a longitudinal sectional view showing schematically apparatus in accordance with present invention.

Referring now to the drawings and, more particularly to FIG. 1 thereof, there is shown apparatus in accordance with the present invention comprising an elongated housing (10) having opposing sidewalls (10A) and (10B) which are generally parallel to a longitudinal axis (12). A socket (14) holds a lamp (16) which is surrounded by parabolic reflector (18) to guide the light from the lamp (16) in direction parallel to the longitudinal axis (12). In a preferred embodiment of the invention, reflector (18) is of a diameter or width of approximately 238 cm and of a length parallel to longitudinal axis (12) of approximately 26 cm.

As shown in FIG. 1, the rear or top end of the housing is sealed by cap (22) having air outlets (20). A cover cap (24), which has a light outlet (26) in the center, fits in the front or bottom end of the housing (10). Light outlet (26) is sealed off on its interior side by a removable, transparent protective disk (28) to protect the interior components of the apparatus.

A box (30), which consists for the most part of perforated sheet metal and which contains two motor-driven blowers (32) (34), arranged one above the other, is attached to one side of housing (10). The air drawn in through the perforated plates of box (30) in the direction of the arrows shown is blown by the blowers through an upper opening (36) near reflector (18) and lamp (16) and through a lower opening (38) into the area of a filter unit, referred to in general as (40), which is to be described further below.

Filter unit (40) is designed as a removable rack type system with a multi-level rack (42), into which the filter disks (44) required for the treatment in question can be inserted parallel to each other.

Between filter unit (40) and light outlet (26), there is a diaphragm device, referred to overall as (46), which is installed in a support wall (48) extending transversely across the housing. Diaphragm device (46) is also explained in greater detail below.

One end (52) of a tape measure (54) is mounted so that it can turn inside cover cap (24) and can be pulled out through an opening (50) in front cover cap (24) of housing (10) to measure the distance between light outlet (26) and the treatment site, and can then be pushed back in the direction of double arrow (56). Of course, in a somewhat more expensive apparatus, the distance can also be measured by means of an electronic distance sensor.

Figure 2:
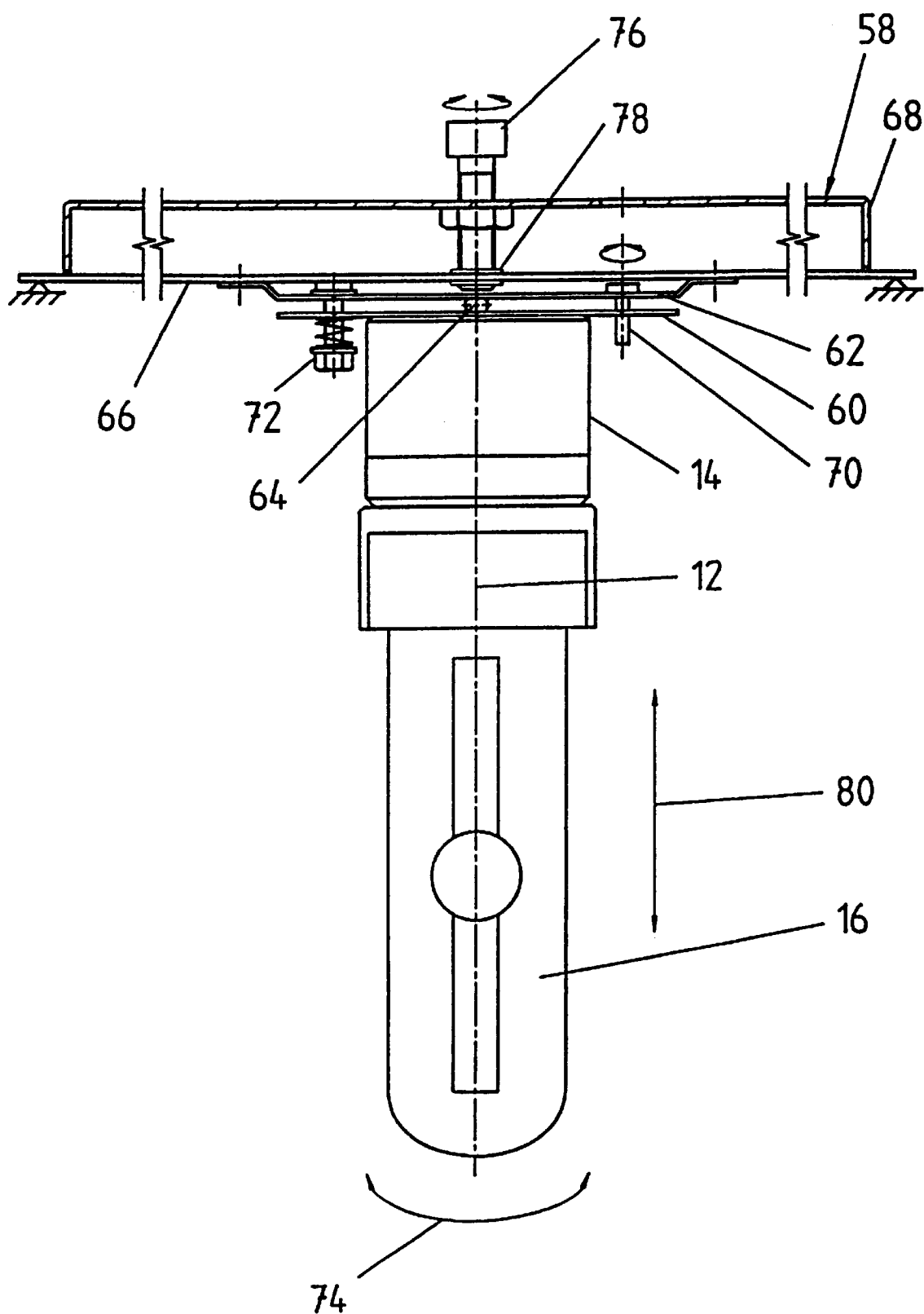
FIG. 2 is a partial side elevational view of the lamp used in apparatus of FIG. 1, together with a focussing device cutaway in the longitudinal direction to show the details more clearly.

In the rear or top section of housing (10), socket (14) of lamp (16) is supported on a focussing device referred to in general as (58). This device is explained in greater detail below on the basis of FIGS. 1 and 2.

First it is to be noted that focussing device (58), lamp (16), reflector (18), and air outlets (20) are positioned with respect to each other so that as little direct light as possible can pass from the lamp (16) through air outlets (20) to the outside. Focussing device (58) has a front intermediate plate (60), to which socket (14) of lamp (16) is attached, and a rear support plate (62), approximately parallel to the front plate. Support plate (62) is attached to a membrane plate (66), only the external edge of which is fastened rigidly to the housing. The rear or top side of the membrane plate is connected in turn to a cup-like bracket plate (68).

Between intermediate plate (60) and support plate (62) there is a ball (64) positioned on longitudinal axis (12). One side of intermediate plate (60) can be adjusted by means of a setscrew (70), mounted in support plate (62), whereas the opposite side is held by a spring-loaded pressure screw (72). Instead of the one setscrew (70) shown, it is also possible to use several setscrews (not shown). By turning setscrew (70), lamp (16) is pivoted in the direction of double arrow (74), around an axis perpendicular to longitudinal axis (12). A setscrew (76) is also provided in bracket plate (68), extending in the longitudinal direction, the adjustable end (78) of which is attached to membrane plate (66). By actuating setscrew (76), therefore, the center of membrane plate (66) and thus support plate (62) attached to it are pushed in the longitudinal direction, as a result of which lamp (16) is shifted in the direction of double arrow (80). Because of the possibility of these adjustments, the lamp can be focussed with extreme accuracy within reflector (18), which is mounted rigidly in the housing.

Figure 3:
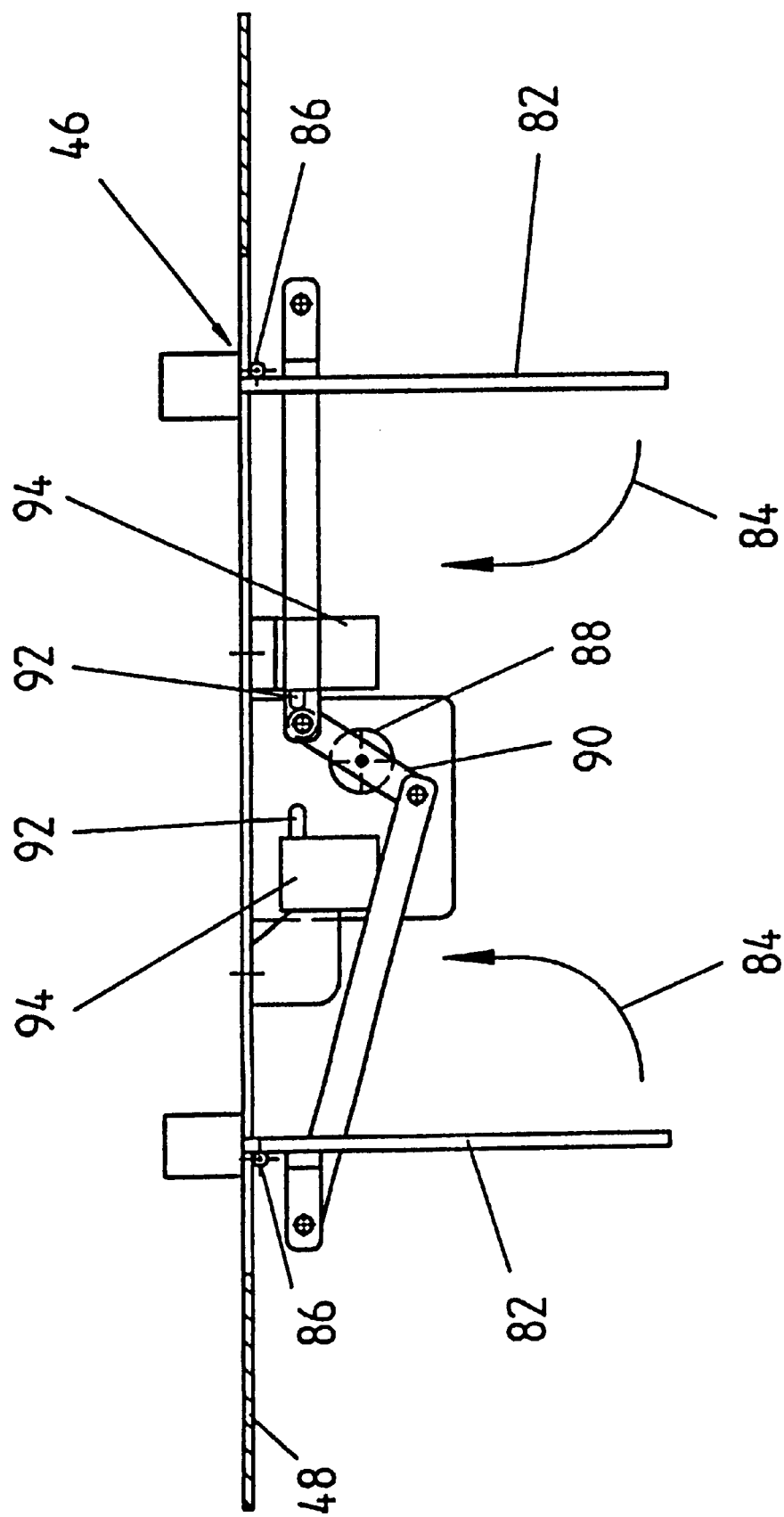
FIG. 3 is a schematic diagrammatic side elevational view of the diaphragm unit used in the apparatus as shown in FIG. 1.

FIG. 3 shows diaphragm device (46) shown in FIG. 1 on an enlarged scale. Diaphragm device (46) has two opaque flaps (82), which, when in the open position according to FIG. 3, are parallel to longitudinal axis (12), and which can be pivoted around their pivot bearings (86) according to arrows (84) into a position (not shown) perpendicular to longitudinal axis (12) to block off the beam path of the apparatus. A crank mechanism (90), driven by a drive motor (88), pivots flaps (82); the two extreme positions are adjusted by means of limit switches (94), actuated by thrust pins (92). Drive motor (88) can be connected to a suitable electronic unit of the apparatus so that it can pivot flaps (82) under accurate time control.

FIGS. 4 and 5 show filter unit (40) used in the apparatus according to FIG. 1 in greater detail. This unit is designed as a standardized filter rack system with a rack (42), which can be attached by suitable brackets (98) to housing (10). Rack (42) has several parallel filter frames (100), each of which has a central opening (102). In addition, strips (104) with a roughly Z-shaped profile are attached to diametrically opposite sides of each filter frame (100); a filter disk (44) can be inserted into them. After insertion, filter disks (44) can be held in place in the insertion direction of the disks by retaining knobs (108), which can be attached either to filter frame (100) or to Z-strips (104).

Figure 6:
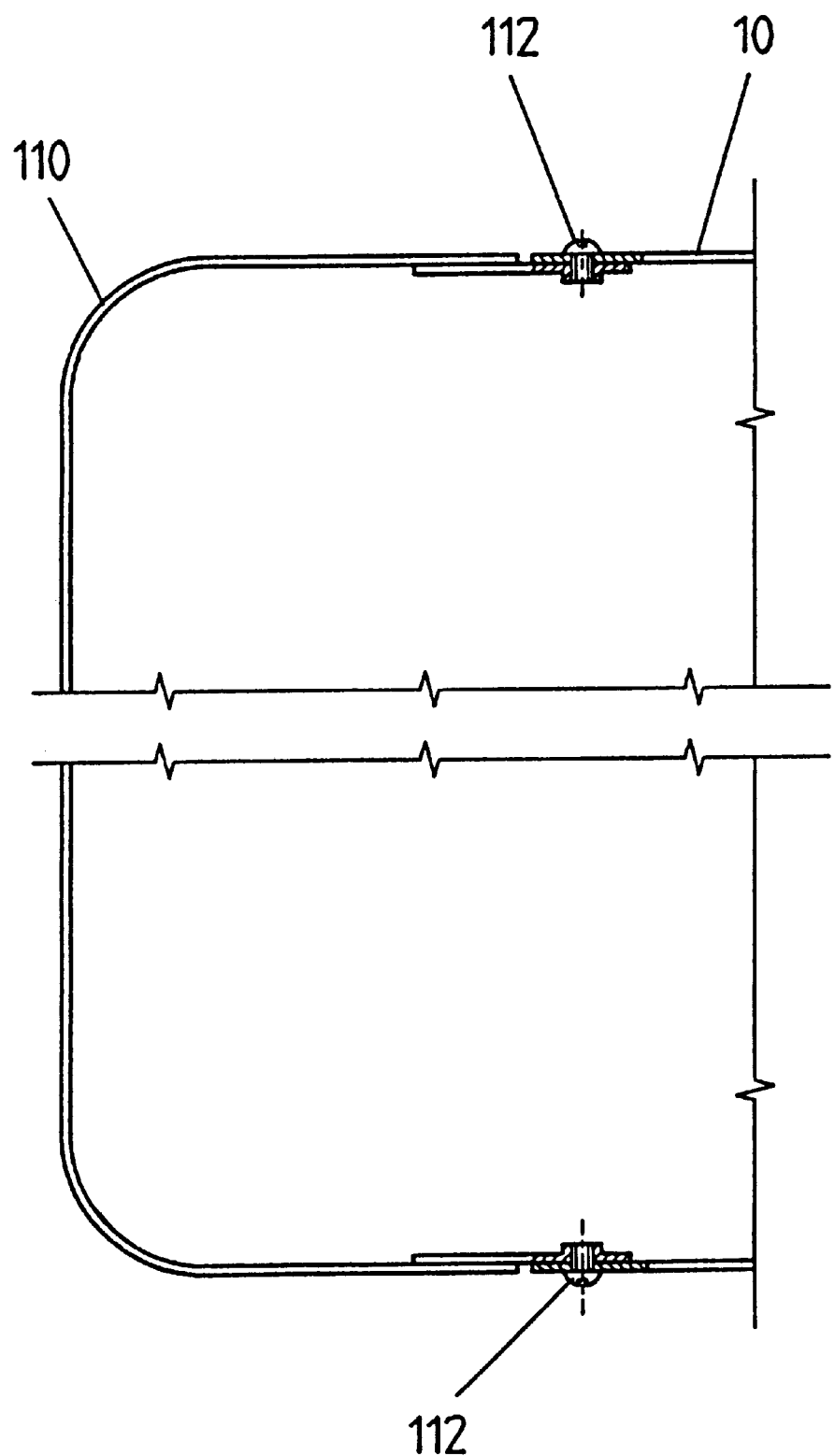
FIG. 6 is a partial view transversely to the longitudinal direction of the housing of apparatus in accordance with the present invention.

So that all apparatus assemblies inside housing (10) can be maintained easily and possibly replaced easily and quickly, a part (110) of the housing wall, extending over the entire length of the housing as shown in FIG. 6, is attached by means of easily removable screws (112) or other removable means of attachment to the rest of housing (10). By removing housing part (110), the interior of housing (10) can be easily made accessible for the purpose indicated and then easily closed again.

In a manner not shown in detail, the entire reflector (18) can be divided in the longitudinal direction into approximately 40–50 segments, which remain edge to edge as they extend from the rear or top end to the front or bottom end of the reflector. The facets can in turn be subdivided into individual subfacets, which have a slight concave curvature in the transverse direction. The overall curvature thus remains parabolic, so that the treatment site is subject to radiation of highly uniform intensity.

Even though a particular embodiment of the invention has been illustrated and described herein, it is not intended to limit the invention and changes and modifications may be made therein within the scope of the following claims.

What is claimed is:

1. Apparatus for photodynamic irradiation comprising a main housing, a lamp mounted in the housing, a reflector surrounding the lamp, a filter unit in the beam path of the lamp, a light outlet at one end of the housing downstream of said filter unit, a perforated blower housing, a pair of blowers in said blower housing operable to circulate air drawn from outside the housing and direct it through discharge openings in the main housing located adjacent the reflector and filter units respectively.

2. Apparatus for photodynamic irradiation comprising a main housing, a lamp mounted in the housing, a reflector surrounding the lamp, a filter unit in the beam path of the lamp, a light outlet at one end of the housing downstream of said filter unit, a perforated blower housing, a pair of blowers in said blower housing operable to circulate air drawn from outside the housing and direct it through discharge openings in the main housing located adjacent the reflector and filter units respectively, a removable housing section for providing access to the interior of the housing for replacement and repair of components of the apparatus.

3. Apparatus for photodynamic irradiation comprising a main housing, a lamp mounted in the housing, a reflector surrounding the lamp, a filter unit in the beam path of the lamp, a light outlet at one end of the housing downstream of said filter unit, a perforated blower housing, a pair of blowers in said blower housing operable to circulate air drawn from outside the housing and direct it through discharge openings in the main housing located adjacent the reflector and filter units respectively, a removable housing section for providing access to the interior of the housing for replacement and repair of components of the apparatus, and a filter unit having a rack which can be removed from the main housing as a unit and having compartments for different filter units.

4. Apparatus according to claim 3 including a dosage device having a computer-controlled diaphragm device (46), which is installed in the beam path inside the light outlet (26) to block the path of the beam.

5. Apparatus according to claim 3, comprising it has a radiation dosimeter, which is designed to be placed at the treatment site, which is connected to the apparatus by a cable, and which controls the dosing device as a function of the radiant energy effectively measured at the treatment site.

6. Apparatus according to claim 3, including a mechanical or electronic distance meter so that the irradiation distance can be adjusted to the desired value.

7. Apparatus according to claim 6, characterized in that the distance meter consists of a pull-out tape measure (52).

8. Apparatus according to claim 3, comprising the light outlet (26) is sealed off by a protective disk (28).

9. Apparatus according to claim 3, including a cap on the housing (10) having air outlets (20), which are positioned in such a way that the amount of light which can emerge from the air outlets (20) is.

10. Apparatus according to claim 3, comprising the reflector (18) has an outside diameter of approximately 28 cm and a length in the longitudinal direction of approximately 26 cm.

11. Apparatus according to claim 3, comprising the reflector (18) is divided in the longitudinal direction into about 40–50 sections, which are subdivided in turn into individual subsection with a slight concave curvature in the transverse direction.

12. Apparatus according to claim 3, comprising with respect to the reflector (18), which is attached rigidly to the housing, the lamp (16) can be focussed both in the direction of the longitudinal axis (12) and perpendicular thereto.

13. Apparatus according to claim 12, characterized in that a focussing device (58), which can be adjusted by means of setscrews (70) (76), is provided for focussing.

14. Apparatus according to claim 3 including a dosage device having a timer-controlled diaphragm device (46), which is installed in the beam path inside the light outlet (26) to block the path of the beam.

15. Apparatus according to claim 14, comprising the diaphragm device consists of a shutter, which can be moved into the path of the beam.

16. Apparatus according to claim 14, comprising the diaphragm device (46) has flaps (82) and actuatable by a crank mechanism (90) driven by an electric motor (88) to position the flaps in the path of the beam.

* * * * *